(12) United States Patent
Copeland

(10) Patent No.: US 6,494,714 B1
(45) Date of Patent: Dec. 17, 2002

(54) METHOD OF MAKING A TOOL TIP AND TOOL TIP

(75) Inventor: Leonard Copeland, York, PA (US)

(73) Assignee: Dentsply Research & Development Corp., Milford, DE (US)

( * ) Notice: Subject to any disclaimer, the term of this patent is extended or adjusted under 35 U.S.C. 154(b) by 0 days.

(21) Appl. No.: 09/490,271

(22) Filed: Jan. 24, 2000

(51) Int. Cl.⁷ .............................................. A61C 17/02
(52) U.S. Cl. .......................................... 433/86; 433/119
(58) Field of Search ................... 433/86, 119; 606/169

(56) References Cited

U.S. PATENT DOCUMENTS

D261,932 S  * 11/1981  Bussiere
5,531,597 A  *  7/1996  Foulkes et al. ............. 433/119
5,567,153 A    10/1996  Foulkes et al. ............. 433/119
5,725,370 A  *  3/1998  Himeno et al. ................ 433/86
5,749,727 A     5/1998  Dao et al. .................... 433/119

* cited by examiner

*Primary Examiner*—Ralph A. Lewis
(74) *Attorney, Agent, or Firm*—Dale R. Lovercheck; James B. Bieber

(57) ABSTRACT

The invention provides a method of making a transducer activated tool tip, comprising, providing a substantially linear tip body having a fluid inlet end and a fluid outlet end. The tip body has an inlet end and a subgingival outlet end. The tip body is bent in a first direction. In the tip body is formed a fluid passageway internal to the tip. The tip body is bent in a second direction, which is opposite to the first direction.

26 Claims, 9 Drawing Sheets

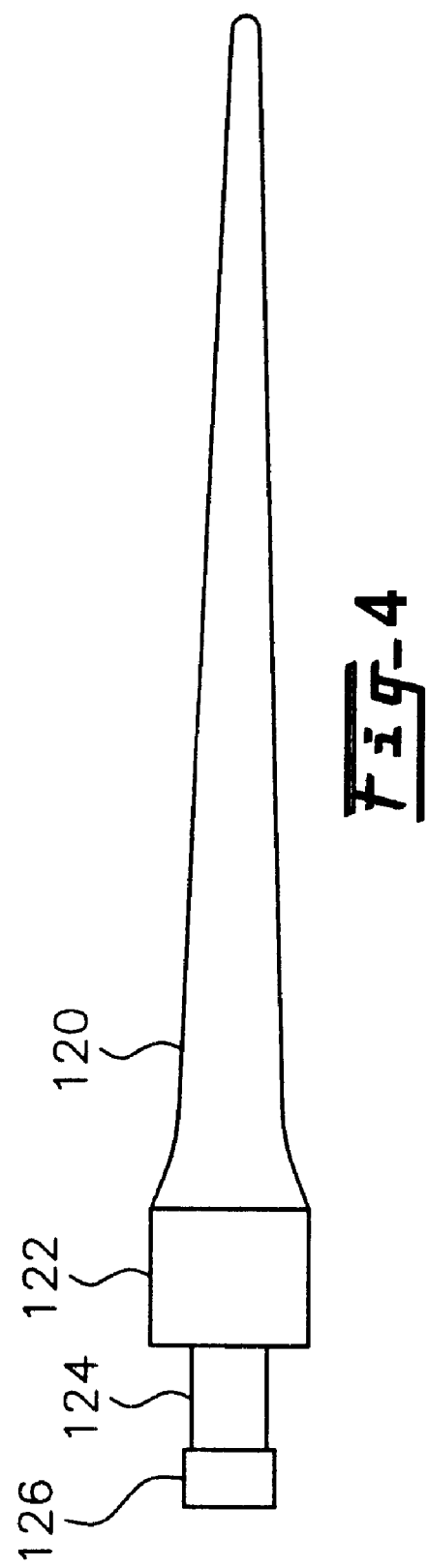

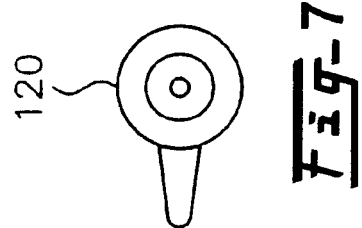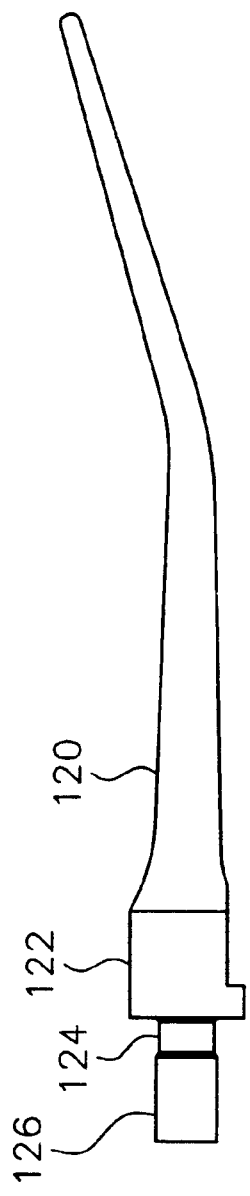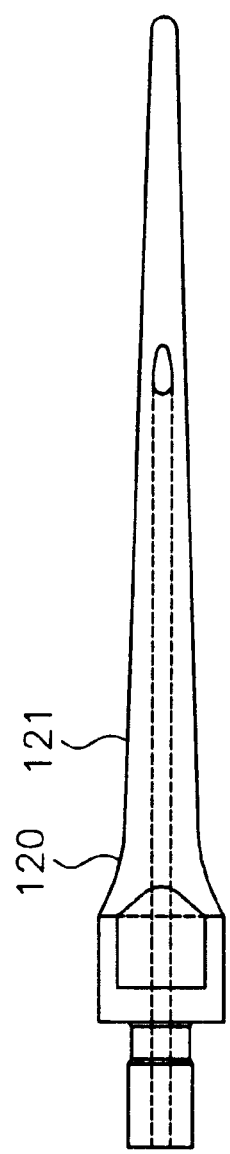

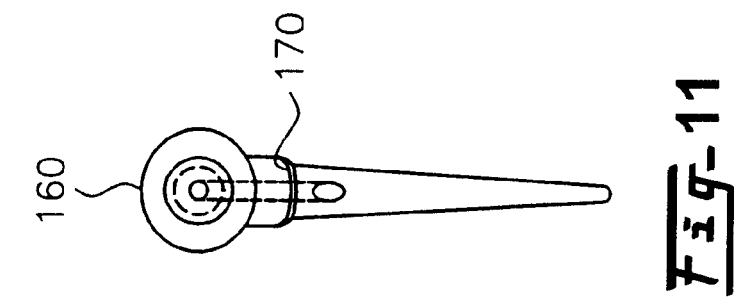
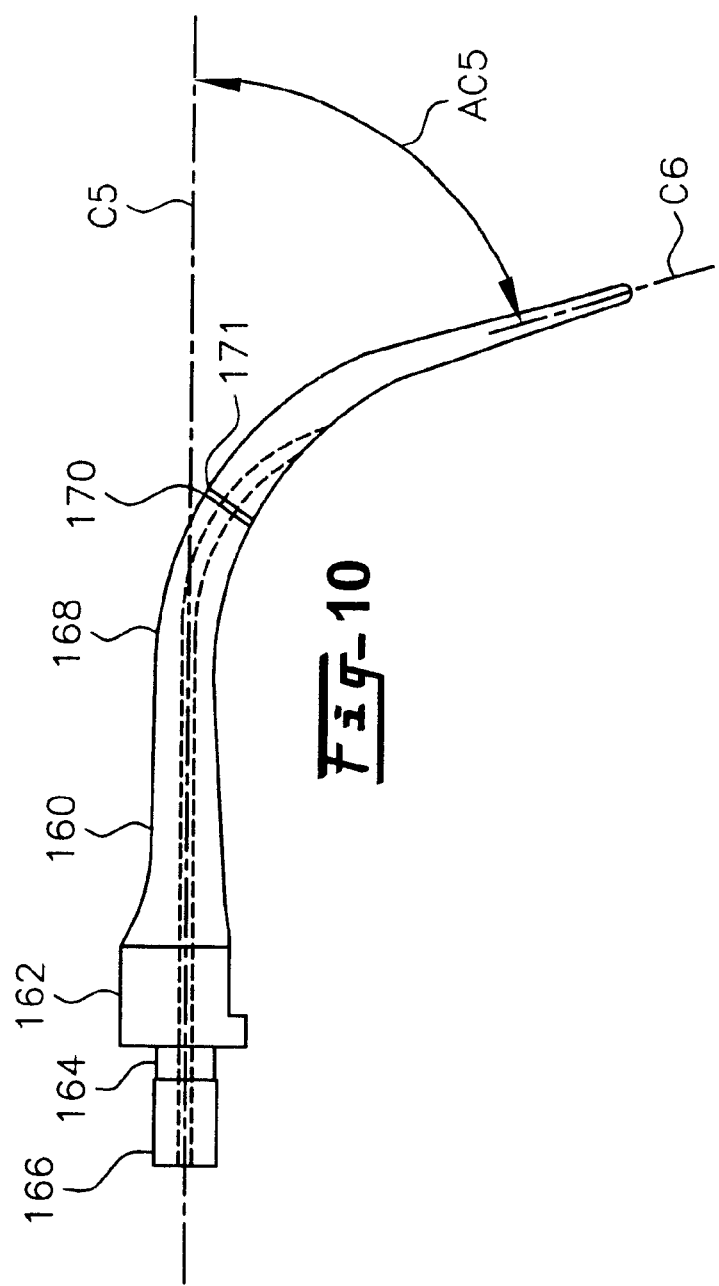

METHOD OF MAKING A TOOL TIP AND TOOL TIP

The invention relates to a transducer activated tool for contacting tooth surfaces and directing a fluid adjacent to the tooth. More particularly, the invention relates to an improved strength ultrasonically activated tool. The tip includes a passageway for directing a fluid onto the dental or tip surfaces. The tip is made by bending the tip at the location for the opening of the passageway, before drilling the passageway. Preferably the end of the tip is adapted for subgingival insertion, and has an outer diameter of less than 0.03 inch within 0.03 inch of the end of the tip. During subgingival insertion the subgingival end of the tip extends between the patient's gum and the subgingival tooth surface, and delivers a focused spray of fluid onto the subgingival tooth surface.

The method of the invention includes bending a tip at least twice. This allows a passageway to be placed in different pre-selected locations. The passageway in a prior art subgingival tip is drilled in the straight tip at a slight angle producing a long exit hole. The passageway in a prior art subgingival tip opens into a hole which crosses high stress areas. The invention allows the hole to be positioned more easily and allows control of the length of the hole independent of the hole location on the tip. The first step is to bend a straight tip which does not have a passageway therethrough. The second step is to drill a passageway through the tip from the fluid inlet end of the tip generally along the straight portion of the tip to the bend. The location of the bend controls the location of the passageway opening (or exit hole) and the bend angle (and bend radius) controls the length of the exit hole. Finally the tip is bent in the opposite direction. The tip may be angled before the final bend is made. Preferably the passageway is concentric relative to the straight tip, the hole could be off center and/or on a slight angle to the tip central line to produce a long exit hole. In addition a short bend with an offset bend gives a very long groove. Alternatively, multiple bends are made in the tip before drilling the passageway to produce various exit hole shapes (or multiple exit holes). Preferably the exit hole is positioned near to the end of the tip. Preferably the exit hole edge is kept away from the high stress area located near the end of the tip and the exit hole is kept short enough to avoid the high stress area near the base of the tip.

Many useful dental instruments employ substantial vibratory motion at a tool tip of the instrument for cleaning, scaling and like operations. The tool tips are designed to produce flexural and longitudinal vibrations with flexural motions of from about 0.02 to 0.2 mm. The tip is typically attached to an electro-mechanical part or section that can be induced to vibrate at high frequency. The instrument is driven by an electronic generator at relatively high frequencies, typically on the order of above 20 kHz, to obtain adequate motion and to minimize objectionable noise since the human hearing threshold is about 18 kHz. The energy generator and related electro-mechanical section may be any one of several types such as electro-dynamic, piezo electric, or magnetostrictive. Design of the tip and its related electro-mechanical components involves combining a number of parameters to produce mechanical resonances (harmonic vibrations) at the driving frequency to produce amplified mechanical motion, particularly at the distal tip end.

Dao et al in U.S. Pat. No. 5,749,727 disclose transducer activated subgingival tool tip, and the disclosure thereof is incorporated herein by reference in its entirety. In use the vibrating tip is guided over and about tooth surfaces by the operator. The tip must be capable of penetrating between teeth and under or below the gingival or gum line. Generally, the tip must be small in cross-section, ideally having a pointed tip with a tapered cross-section extending about 2.5 to 5 mm back from the distal tip end to allow adequate access between teeth and gingival. More preferably the tapered cross-section extends about 10 mm from the distal tip end.

The prior art does not provide a method of making an insert for an ultrasonically activated subgingival tooth cleaning tool, comprising: bending a solid metal tip to form a bend at a location for an opening of a passageway, then drilling the passageway through the solid metal tip to form a tip having a passageway having an opening at the bend, as is provided by the present invention.

The prior art does not provide a method of making a transducer activated tool tip, comprising, providing a substantially linear tip body having a fluid inlet end and a fluid outlet end, wherein the tip body is bent in a first direction so that a centerline through the fluid outlet end intersects a centerline through the fluid inlet end at an angle greater than 5 degrees and then in the tip body is formed a fluid passageway internal to the tip, having an inlet end and a subgingival outlet end, then the tip body is bent in a second direction so that a centerline through the fluid outlet end intersects a centerline through the fluid inlet end at an angle of substantially 0 degrees, and the tip body is bent further in the second direction so that the centerline through the fluid outlet end intersects the centerline through the fluid inlet end at an angle greater than 5 degrees, as is provided by the present invention.

OBJECTS OF THE INVENTION

It is an object of the invention to provide a method of making an insert for an ultrasonically activated subgingival tooth cleaning tool, comprising: bending a solid metal tip to form a bend at a location for an opening of a passageway, then drilling the passageway through the solid metal tip to form a tip having a passageway having an opening at the bend.

It is an object of the invention to provide a transducer activated tool for contacting subgingival tooth surfaces and directing a fluid adjacent to the subgingival surfaces, comprising an activated tip has a fluid inlet end, a subgingival outlet end, and a fluid passageway wall internal to the tip. The fluid passageway wall has an average passageway diameter. The fluid passageway wall ends at an edge providing a fluid discharge orifice formed in a discharge side of the subgingival outlet end of the tip. The subgingival outlet end has an opposite side positioned opposite to the discharge side. The discharge side has a discharge side outer surface whereby a first line tangential to the discharge side outer surface of the fluid inlet end, and a second line tangential to the discharge side outer surface of the subgingival outlet end intersect to form an angle of less than 180 degrees facing outwardly from the discharge side outer surface.

It is an object of the invention to provide a transducer activated tool for contacting tooth surfaces and directing a fluid adjacent to the surfaces, comprising an activated tip has a fluid inlet end, a outlet end, and a fluid passageway wall internal to the tip, the activated tip has a tip centerline, the fluid passageway wall ends at an edge providing a fluid discharge orifice formed in a discharge side of the outlet end of the tip, the outlet end has an opposite side positioned opposite to the discharge side. The discharge side has a discharge side outer surface whereby a line uniformly offset from the tip centerline on the discharge side outer surface forms an angle of less than 180 degrees outwardly from the discharge side outer surface. The transducer activated tool is formed from a preformed body of the tool wherein the opposite side has an opposite side outer surface whereby a line uniformly offset from the tip centerline on the opposite side outer surface forms an angle of less than 180 degrees outwardly from the opposite side outer surface.

It is an object of the invention to provide a transducer activated subgingival tool for contacting subgingival tooth surfaces and directing a fluid adjacent to the surfaces, comprising an activated tip has a fluid inlet end, a subgingival outlet end, and a fluid passageway wall internal to the tip, the fluid passageway wall ends at an edge providing a fluid discharge orifice formed in a discharge side of the outlet end of the tip. The subgingival outlet end has an opposite side positioned opposite to the discharge side. The discharge side has a discharge side outer surface whereby a line on the discharge side outer surface forms an angle of less than 180 degrees outwardly from the discharge side outer surface. The transducer activated subgingival tool is formed from a preform of the tool. The opposite side has an opposite side outer surface whereby a line on the opposite side outer surface forms an angle of less than 180 degrees outwardly from the opposite side outer surface.

It is an object of the invention to provide a preformed tool for making a transducer activated subgingival tool for contacting subgingival tooth surfaces and directing a fluid adjacent to the surfaces, comprising an activated tip has a fluid inlet end, a subgingival outlet end, and a fluid passageway wall internal to the tip formed in the inlet end generally along the longitudinal center axis of the inlet end of the tip. The subgingival outlet end has a discharge side and an opposite side. The opposite side is opposite to the discharge side. The opposite side has an outer surface which forms an angle of less than 180 degrees. The fluid passageway has a central axis which is substantially on the center axis of the inlet end of the tip. The fluid passageway wall ends at an edge providing a fluid discharge orifice formed in the discharge side of the tip.

It is an object of the invention to provide an insert for an ultrasonically activated subgingival tool of a generally axially elongated cylindrical structure comprising a handpiece including a coil for generating an electromagnetic field, the insert is vibrated at high frequency in longitudinal motion in response to the coil, the insert comprising a magnetostrictive element; a connecting body, axially transmitting the high frequency motion from the ultrasonic magnetostrictive element; and a tip, axially attached to the connecting body, that receives the longitudinal motion, has distal surfaces shaped to contact a subgingival tooth surface. The tip comprises a fluid passageway wall extending internally through a substantial portion of the tip, formed generally along the longitudinal center axis of the tip, the tip has an inlet end and a subgingival outlet end, the subgingival end is shaped to contact the subgingival tooth surfaces without damaging the adjacent gum, a 0.03 inch length of the subgingival end of the tip within 0.03 inch of terminus has one or more outer diameters, each of the diameters is is less than 0.03 inch. The fluid passageway wall has an average diameter, an outlet opening diameter, and opens into a groove channel has a groove channel length. The groove channel length is more than 0.5 and less than three times the outlet opening diameter. Preferably the tip passageway orifice exits within a range of about 2–14 mm from the fluid outlet end of the tip.

It is an object of the invention to provide a method of making an insert for an ultrasonically activated subgingival tooth cleaning tool, comprising providing a preformed tool comprising an activated tip has a fluid inlet end, a subgingival outlet end, and a fluid passageway wall internal to the tip, the fluid passageway wall ends at an edge providing a fluid discharge orifice formed in a discharge side of the tip, the fluid discharge orifice is in the discharge side, the tip has an opposite side, the opposite side is opposite to the discharge side, the opposite side has an outer surface which forms an angle of less than 180 degrees outwardly from the opposite side, bending the tip whereby a first line tangential to the discharge side outer surface of the fluid inlet end, and a second line tangential to the discharge side outer surface of the subgingival outlet end intersect to form an angle of less than 180 degrees facing outwardly from the discharge side outer surface.

It is an object of the invention to provide a method of making a transducer activated tool tip, comprising, providing a substantially linear tip body has a fluid inlet end and a fluid outlet end, bending the tip body in a first direction so that a centerline through the fluid outlet end intersects a centerline through the fluid inlet end at an angle greater than 5 degrees, and forming in the tip body a fluid passageway internal to the tip, has an inlet end and a subgingival outlet end, the subgingival outlet end of the tip has a longest cross-sectional dimension of less than 0.03 inch; bending the tip body in a second direction so that a centerline through the fluid outlet end intersects a centerline through the subgingival outlet end at an angle of substantially 0 degrees, continuing to bend the tip body in the second direction so that the centerline through the fluid inlet end intersects the centerline through the subgingival outlet end at an angle greater than 5 degrees.

It is an object of the invention to provide a method of making a transducer activated tool tip for contacting subgingival tooth surfaces and directing a fluid adjacent to the surfaces, comprising, providing a substantially linear tip body has a fluid inlet end and a fluid outlet end, shaping the fluid outlet end to form distal surfaces for contacting the subgingival tooth surfaces; bending the tip body in a first direction so that a centerline through the fluid outlet end intersects a centerline through the fluid inlet end at an angle greater than 5 degrees, and forming in the tip body a fluid passageway internal to the tip, has an inlet end and a subgingival outlet end, the subgingival end extending distally from a step in the outer surface of the tip and is shaped to contact the tooth surfaces, the subgingival outlet end of the tip has a longest cross-sectional dimension of less than 0.03 inch; the passageway wall is offset from the centerline of the tip whereby a discharge orifice is formed by an edge of the passageway wall at a side of the tip, bending the tip body in a second direction so that a centerline through the fluid outlet end intersects a centerline through the fluid inlet end at an angle of substantially 0 degrees, continuing to bend the tip body in the second direction so that the centerline through the fluid outlet end intersects the centerline through the fluid inlet end at an angle greater than 5 degrees.

SUMMARY OF THE INVENTION

The invention provides a method of making an insert for an ultrasonically activated subgingival tooth cleaning tool, comprising: bending a solid metal tip to form a bend at a location for an opening of a passageway, then drilling the passageway through the solid metal tip to form a tip having a passageway having an opening at the bend.

The invention provides a transducer activated tool for contacting subgingival tooth surfaces and directing a fluid adjacent to the subgingival surfaces, comprising an activated tip has a fluid inlet end, a subgingival outlet end, and a fluid passageway wall internal to the tip. The fluid passageway wall has an average passageway diameter. The fluid passageway wall ends at an edge providing a fluid discharge orifice formed in a discharge side of the subgingival outlet end of the tip. The subgingival outlet end has an opposite side positioned opposite to the discharge side. The discharge side has a discharge side outer surface whereby a first line tangential to the discharge side outer surface of the fluid inlet end, and a second line tangential to the discharge side outer surface of the subgingival outlet end intersect to form an angle of less than 180 degrees facing outwardly from the discharge side outer surface.

The invention provides a transducer activated tool for contacting tooth surfaces and directing a fluid adjacent to the surfaces, comprising an activated tip has a fluid inlet end, a outlet end, and a fluid passageway wall internal to the tip, the activated tip has a tip centerline, the fluid passageway wall ends at an edge providing a fluid discharge orifice formed in a discharge side of the outlet end of the tip, the outlet end has an opposite side positioned opposite to the discharge side. The discharge side has a discharge side outer surface whereby a line uniformly offset from the tip centerline on the discharge side outer surface forms an angle of less than 180 degrees outwardly from the discharge side outer surface. The transducer activated tool is formed from a preformed body of the tool wherein the opposite side has an opposite side outer surface whereby a line uniformly offset from the tip centerline on the opposite side outer surface forms an angle of less than 180 degrees outwardly from the opposite side outer surface.

The invention provides a transducer activated subgingival tool for contacting subgingival tooth surfaces and directing a fluid adjacent to the surfaces, comprising an activated tip has a fluid inlet end, a subgingival outlet end, and a fluid passageway wall internal to the tip, the fluid passageway wall ends at an edge providing a fluid discharge orifice formed in a discharge side of the outlet end of the tip. The subgingival outlet end has an opposite side positioned opposite to the discharge side. The discharge side has a discharge side outer surface whereby a line on the discharge side outer surface forms an angle of less than 180 degrees outwardly from the discharge side outer surface. The transducer activated subgingival tool is formed from a preform of the tool. The opposite side has an opposite side outer surface whereby a line on the opposite side outer surface forms an angle of less than 180 degrees outwardly from the opposite side outer surface.

The invention provides a preformed tool for making a transducer activated subgingival tool for contacting subgingival tooth surfaces and directing a fluid adjacent to the surfaces, comprising an activated tip has a fluid inlet end, a subgingival outlet end, and a fluid passageway wall internal to the tip formed in the inlet end generally along the longitudinal center axis of the inlet end of the tip. The subgingival outlet end has a discharge side and an opposite side. The opposite side is opposite to the discharge side. The opposite side has an outer surface which forms an angle of less than 180 degrees. The fluid passageway has a central axis which is substantially on the center axis of the inlet end of the tip. The fluid passageway wall ends at an edge providing a fluid discharge orifice formed in the discharge side of the tip.

The invention provides an insert for an ultrasonically activated subgingival tool of a generally axially elongated cylindrical structure comprising a handpiece including a coil for generating an electromagnetic field, the insert is vibrated at high frequency in longitudinal motion in response to the coil, the insert comprising a magnetostrictive element; a connecting body, axially transmitting the high frequency motion from the ultrasonic magnetostrictive element; and a tip, axially attached to the connecting body, that receives the longitudinal motion, has distal surfaces shaped to contact a subgingival tooth surface. The tip comprises a fluid passageway wall extending internally through a substantial portion of the tip, formed generally along the longitudinal center axis of the tip, the tip has an inlet end and a subgingival outlet end, the subgingival end is shaped to contact the subgingival tooth surfaces without damaging the adjacent gum, a 0.03 inch length of the subgingival end of the tip within 0.03 inch of terminus has one or more outer diameters, each of the diameters is less than 0.03 inch. The fluid passageway wall has an average diameter, an outlet opening diameter, and opens into a groove channel has a groove channel length. The groove channel length is more than 0.5 and less than three times the outlet opening diameter. Preferably the tip passageway orifice exits within a range of about 2–14 mm from the fluid outlet end of the tip.

The invention provides a method of making an insert for an ultrasonically activated subgingival tooth cleaning tool, comprising providing a preformed tool comprising an activated tip has a fluid inlet end, a subgingival outlet end, and a fluid passageway wall internal to the tip, the fluid passageway wall ends at an edge providing a fluid discharge orifice formed in a discharge side of the tip, the fluid discharge orifice is in the discharge side, the tip has an opposite side, the opposite side is opposite to the discharge side, the opposite side has an outer surface which forms an angle of less than 180 degrees outwardly from the opposite side, bending the tip whereby a first line tangential to the discharge side outer surface of the fluid inlet end, and a second line tangential to the discharge side outer surface of the subgingival outlet end intersect to form an angle of less than 180 degrees facing outwardly from the discharge side outer surface.

The invention provides a method of making a transducer activated tool tip, comprising, providing a substantially linear tip body has a fluid inlet end and a fluid outlet end, bending the tip body in a first direction so that a centerline through the fluid outlet end intersects a centerline through the fluid inlet end at an angle greater than 5 degrees, and forming in the tip body a fluid passageway internal to the tip, has an inlet end and a subgingival outlet end, the subgingival outlet end of the tip has a longest cross-sectional dimension of less than 0.03 inch; bending the tip body in a second direction so that a centerline through the fluid outlet end intersects a centerline through the fluid inlet end at an angle of substantially 0 degrees, continuing to bend the tip body in the second direction so that the centerline through the fluid outlet end intersects the centerline through the fluid inlet end at an angle greater than 5 degrees.

BRIEF DESCRIPTION OF THE DRAWINGS

FIG. 4 is a side view of a tip of solid metal for use in making a subgingival tip in accordance with a preferred embodiment of the invention.

FIG. 5 is a side view after bending the tip of solid metal shown in FIG. 4.

FIG. 6 is a bottom view after drilling a passage through the tip shown in FIG. 5.

FIG. 7 is an end view of the tip shown in FIG. 6.

FIG. 10 is a side view of a subgingival tip in accordance with a preferred embodiment of the invention.

FIG. 11 is an end view of the tip shown in FIG. 10.

DETAILED DESCRIPTION OF PREFERRED EMBODIMENTS

The invention is now described with more particular reference to FIGS. 1–16. In general, a transducer activated tool for contacting tooth surfaces and directing a fluid onto the tooth. A principal element of the invention is an activated tip comprising distal surfaces that are shaped to contact the tooth surfaces. Additionally, the tip includes a fluid passageway internal to the tip extending substantially along the longitudinal center axis of the tip but offset such that a fluid discharge orifice is formed displaced from the distal tip axis. A connecting body connects the tip to an activating transducer and a fluid source is connected to the tool to supply a flow of fluid through the fluid passageway such that it discharges from the passageway orifice.

A key advantage of the activated tip of the invention is that the fluid passageway and its discharge orifice arrangement relate to the fluid outlet end of the tip such that the arrangement does not weaken the tip distal portion by removing metal or materials of construction at a critical portion of the tip at its points of maximum stress. Secondly, the fluid discharge orifice of tips of the invention is not located at a node of flexural motion such that tip breakage is reduced.

Figure 1:
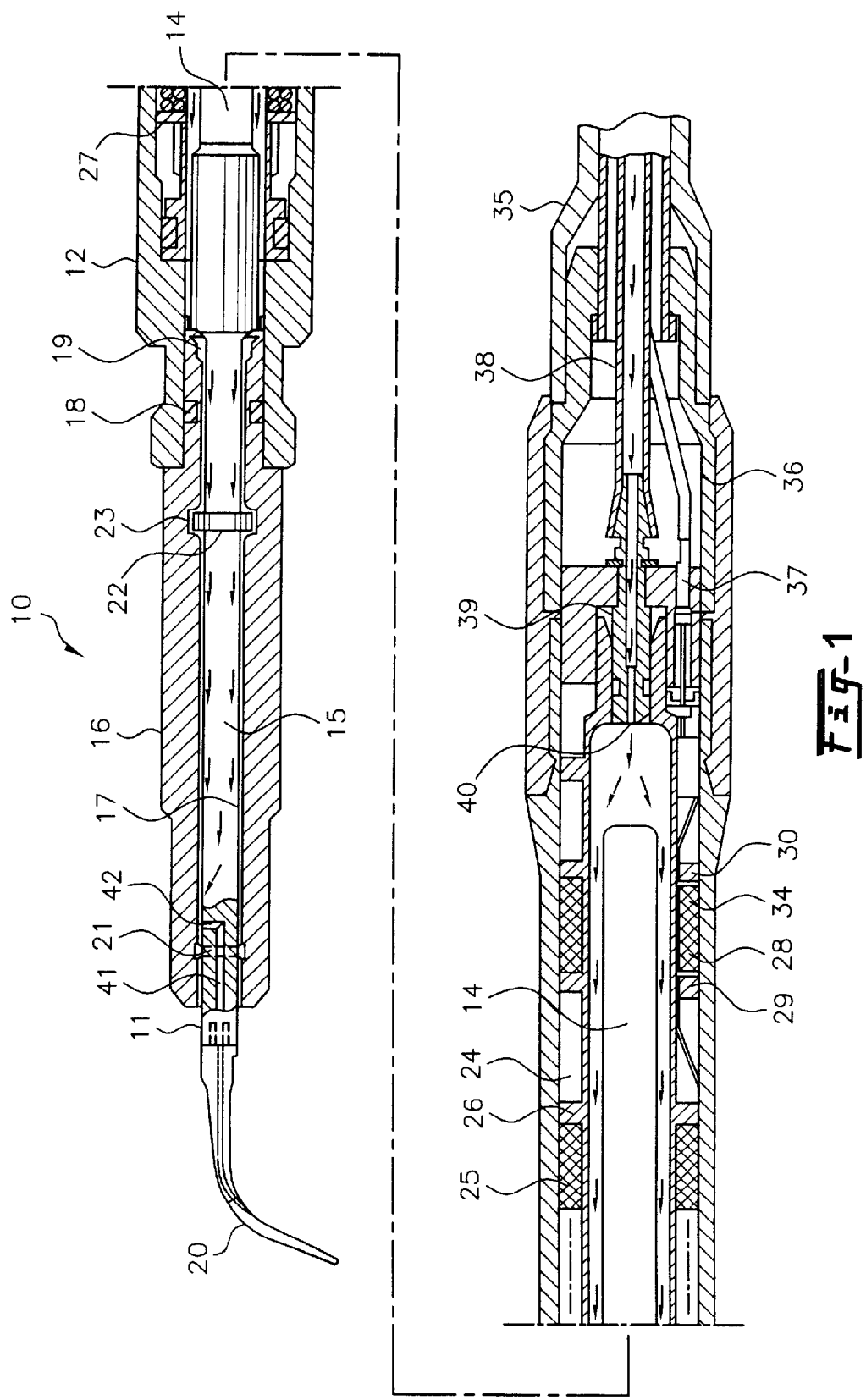
FIG. 1 is a sectional view of an ultrasonically activated tool tip of the invention as a component of a dental tool insert in combination with a handpiece.
Figure 2:
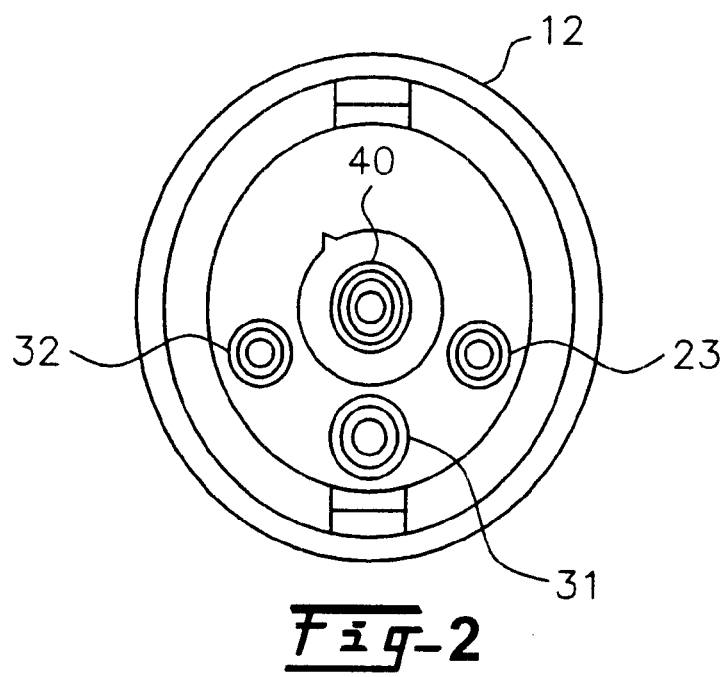
FIG. 2 is an end view of the handpiece component with the electrical/fluid supply connectors detached.
Figure 3:
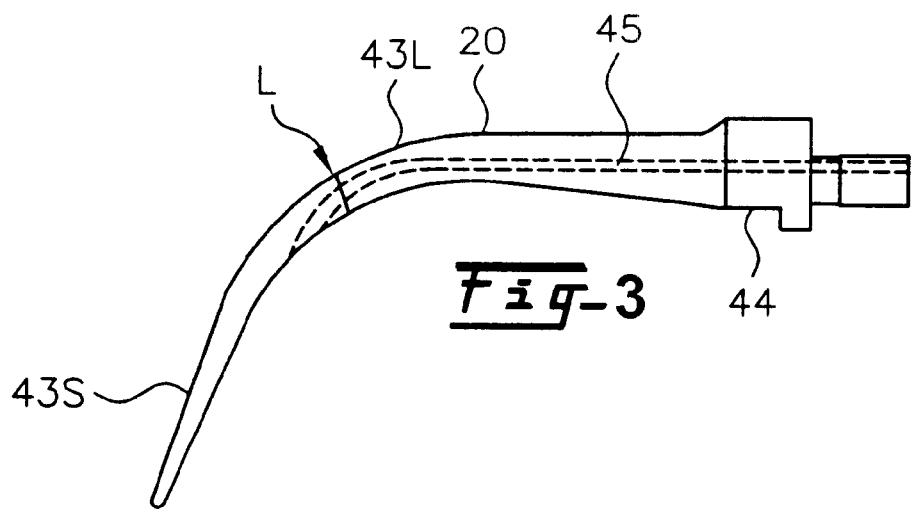
FIG. 3 is an enlarged sectional view of a tip of the invention having a fluid passageway having a centerline which intersects the tip centerline at an angle.

Referring to the drawings, FIGS. 1 and 2 show a preferred embodiment of the invention wherein the tip is a component of an ultrasonically activated tool 10 for dental use, comprising a dental tool insert 11 in combination with a handpiece 12.

The general configuration of the tool of the invention is well known in the art and is similar to the ultrasonic device described by Perdreaux in Re. 30,536. The tool insert 11 includes a tool tip 20, a key element of the invention which will be described in more detail below, and a magnetostrictive element 14, joined by a connecting body 15. A portion of the connecting body 15 is enclosed in a sleeve 16 which is formed to enclose a portion of the connecting body 15 such that the connecting body is free to transmit energy to the tip. In addition, the sleeve forms an annular passageway 17 permitting fluid flow to the tip 20. A reduced end cross-section of the sleeve 16 permits it to be removably inserted into the housing 12. An O-ring 18 fits into a groove cut into the sleeve providing a retaining, frictional fit therebetween. The internal posterior face 19 of this section is countersunk to facilitate fluid flow about the connecting body. At the fluid inlet end of the sleeve, its internal bore is fitted with a groove and O-ring 21 which, in combination with the connecting body 15, provide a seal for preventing fluid from flowing from the assembled sleeve and connecting body.

The connecting body 15 functions as an acoustical impedance transformer for transporting energy from the magnetostrictive stack 14 to the work tool tip 20. As is well known in the art, the connecting body 15 varies in cross-section along its longitudinal length which varies the amplitude of mechanical vibration, with the ultimate object of obtaining a desired amplitude magnification at the operating tip that is useful for performing a task on a tooth. These principals are well described by Banko in U.S. Pat. No. 3,930,173, which is incorporated herein by reference.

The connecting body 15 includes a ring 22 brazed or machined onto its shaft adjacent to the nodal point and sized to fit loosely into a corresponding groove 23 cut into the sleeve interior surface. The ring 22 includes a single key (not shown) on its outer circumference that fits into one of two semicircular bypasses (not shown) cut longitudinally into the interior surfaces of the bore, 180 degrees apart from each other and centered with a radius or altitude of the groove 23. The key is held in one of the bypasses after assembly which serves as a retainer for the key while the other bypass provides a path for fluid flow around the ring.

Brazed or otherwise firmly attached to the connecting body 15 is the magnetostrictive vibrator or stack 14 which is preferably formed of a metal alloy such as permanickel, nickel or other alloys that possess high tensile strength and are highly magnetostrictive in character.

The housing or handpiece 12 includes a coil unit 24 that produces a magnetic field for inducing motion longitudinally to the insert 11 through the magnetostrictive stack 14. The coil unit includes a drive coil 25 that is connected to an alternating current source. The drive coil 25 is wound in a double coil between retaining flanges 26, 27 and provides an electromagnetic field in the handpiece 12. A feedback coil 28 of fine wire is provided to register voltage developed by the insert in the electromagnetic field and the handpiece. The feedback coil is a winding of five layers of wire, between flanges 29, 30, and is connected to ground terminal 31 and terminal 32, shown in FIG. 2. A bucking coil 34, of heavier wire than the feedback coil is wound in one layer over the feedback coil and is designed to minimize transformer coupling between the drive coil and the feedback coil. The bucking coil and drive coil are connected between terminals 31 and 33 in one continuous wire. The drive coil is attached to terminal 33 and, using a right hand turn for example, is wound from flange 26 to flange 27 and back. The end of the wire is then connected to terminal 31. The bucking coil and drive coil are wired in series and are wound in opposite direction and are therefore electromagnetically 180 degrees out of phase. The bucking coil is electrically insulated from the feedback coil.

Electrical power and fluid are supplied to the instrument by means of a cable 35, including a plug attachment 36 that connects to the handpiece. The electrical supply is connected through three electrical pin connectors 37 (only one shown) that mate with the handpiece receptacle terminals shown in FIG. 2. Pin connectors connected to the terminals 32, 33 provide power to the coil and register feedback while a pin connected to a grounded terminal 31 acts as a common ground. The cable 35 also includes a fluid conduit 38 and a connector fitting 39 for attachment to the body of the handpiece. The conduit supplies fluid to the handpiece, and, ultimately, the tool tip 20, through a passageway 40, initially into contact with the magnetostrictive element 14 to provide cooling.

At the fluid outlet end of the connecting body 15, the connecting body is counter-bored to form a central axial longitudinal passageway 41 for fluid flow to the tip 20. A radial boring 42 in the connecting body 15 at the interior terminus of the fluid passageway boring connects the central passageway 41 with the interior of the sleeve 16 to collect fluid flowing from (shown in the drawings as small arrows) about the magnetostrictive element. The radial boring 42 is located on the internal side of the O-ring gasket 21 so that flow of fluid from the handpiece interior is only from the central bore 41 out of the connecting body.

The tip 20, the operative portion of the ultrasonically activated tool, comprises a smaller diameter distal tip portion 43S for contacting tooth surfaces, larger diameter portion 43L and a shank portion 44 that is secured to the connecting body 15. Smaller diameter portion 43S intersects larger diameter portion 43L at a tip surface angle transition line L. The connecting body includes a counter bore for receiving the tip shank 44 which may be secured by brazing, mating threads or the like. A fluid passageway 45, described in detail below, formed interior to the tip element or body, exits through an internal or side wall in the tip to provide a fluid discharge orifice 46.

Referring to FIG. 1, in operation, an alternating current impressed upon the coil unit 24 described above creates an alternating magnetic field in the handpiece portion 12 surrounding the magnetostrictive stack 14. The electromagnetic field vibrationally excites the magnetostrictive stack 14, imparting longitudinal motion at ultrasonic frequency to the connecting body 15 and tip 20 connected thereto. As discussed above, the longitudinal motion causes the fluid outlet end 43 of the tip 20 to vibrate flexurally to produce a motion useful for performing a task on a tooth, such as, for example, cleaning a tooth. Simultaneously, a flow of cooling/irrigating fluid flows into the handpiece chamber containing the magnetostrictive stack, cooling the stack and passing therefrom into the annular space between the sleeve 16 and connecting body 15. The fluid leaves the connecting body discharge passageway and flows into the tip passageway 45, discharging from the discharge orifice 46 onto the tooth surfaces, providing cooling and cleaning or other desired effects depending upon the character of the fluid applied and tooth operated on. The tips shown in FIGS. 8–16 are adapted to be used in place of tip 20 in handpiece 12.

Figure 8:
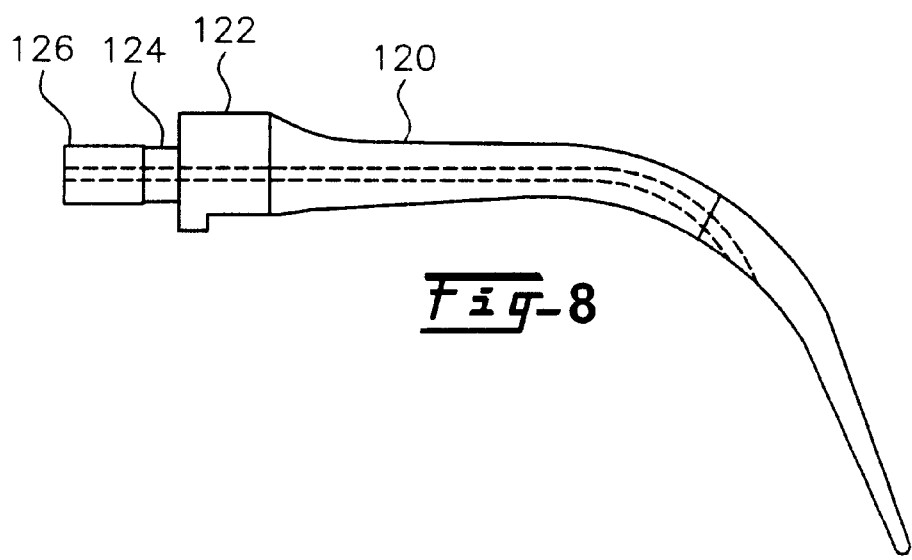
FIGS. 8 and 9 are side and bottoms views respectively after bending the tip shown in FIGS. 6 and 7 to form a subgingival tip in accordance with a preferred embodiment of the invention.
Figure 9:
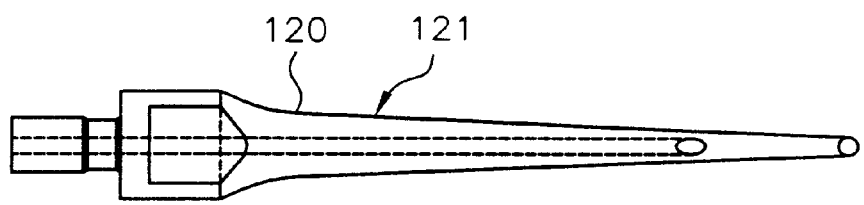

With more particular reference to FIGS. 4–9 subgingival tip 120 is seen. Tip 120 has flange 122 joined by connecting member 124 to flange 126. Initially tip 120 is solid metal and extends along a linear central axis as shown in FIG. 4. Then tip 120 is bent as shown in FIG. 5. A passageway is then drilled along the linear portion of the central axis of tip 120 as shown in FIG. 6. Then tip 120 is bent as shown in FIGS. 8 and 9.

In a preferred embodiment of the invention tip 120 has upper body end joined along shoulder (or step) to lower body end. The shoulder has a curved side wall. Preferably the step intersects the passageway wall edge which forms an orifice.

With more particular reference to FIGS. 10 and 11 subgingival tip 160 is seen. Tip 160 has step 170, flange 162 joined by connecting member 164 to flange 166. Step 170 has curved side 171. Step 170 is formed as disclosed by Dao et al in U.S. Pat. No. 5,749,727. Tip central axis $C5$ intersects passageway central axis $C6$ at angle $AC5$. Tip 160 is preferably made by bending, drilling and bending as discussed above in reference to FIGS. 4–9.

Figure 12:
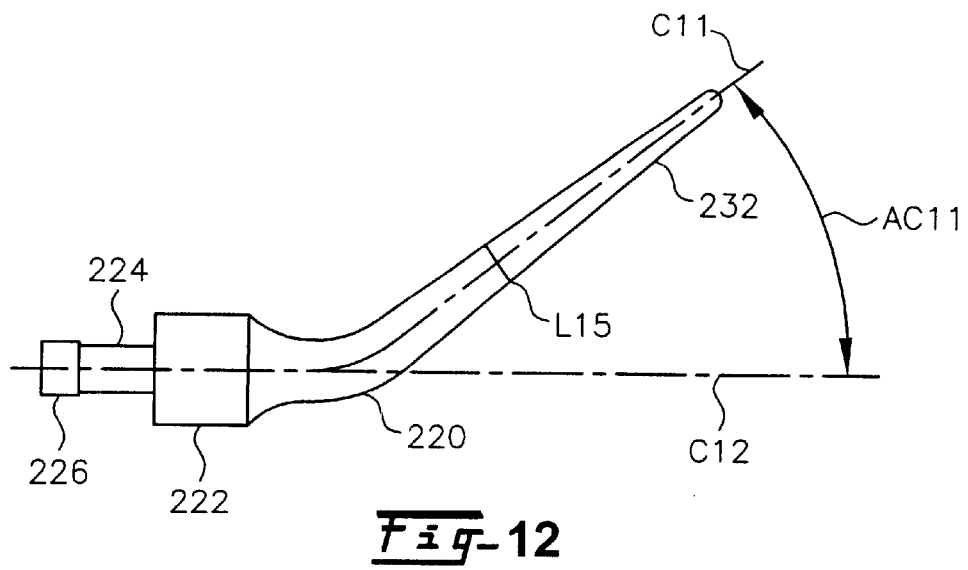
FIG. 12 is a side view of a subgingival tip in accordance with a preferred embodiment of the invention.
Figure 13:
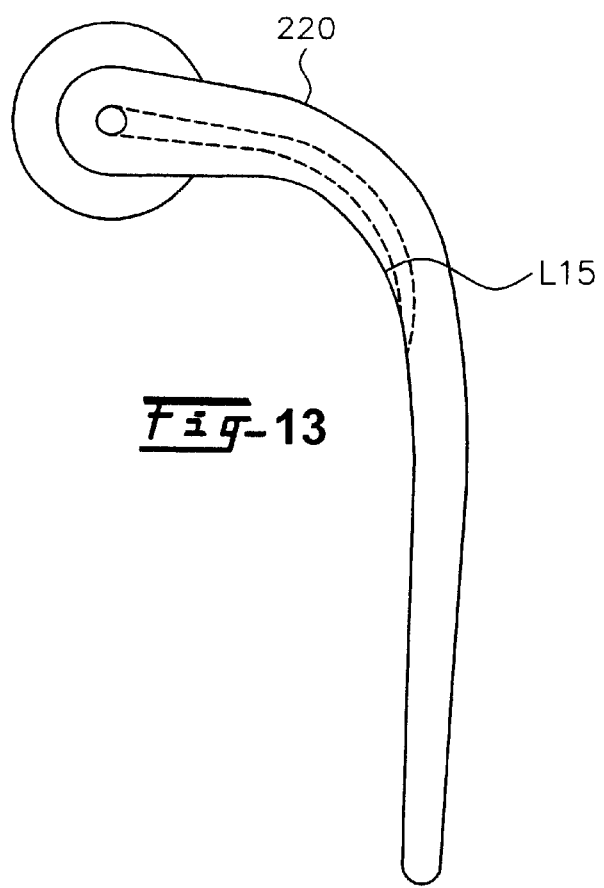
FIG. 13 is an end view of the subgingival tip shown in FIG. 12.

With more particular reference to FIGS. 12 and 13 subgingival tip 220 is seen. Tip 220 has step L15, flange 222 joined by connecting member 224 to flange 226. Step L15 is formed as disclosed by Dao et al in U.S. Pat. No. 5,749,727. Tip central axis $C11$ intersects central axis $C12$ of an internal passageway at angle $AC11$. Tip 220 is preferably made by bending a first bend, drilling and bending a second bend as discussed above in reference to FIGS. 4–9, then bending a third bend to form the shape shown in FIGS. 12 and 13.

Figure 14:
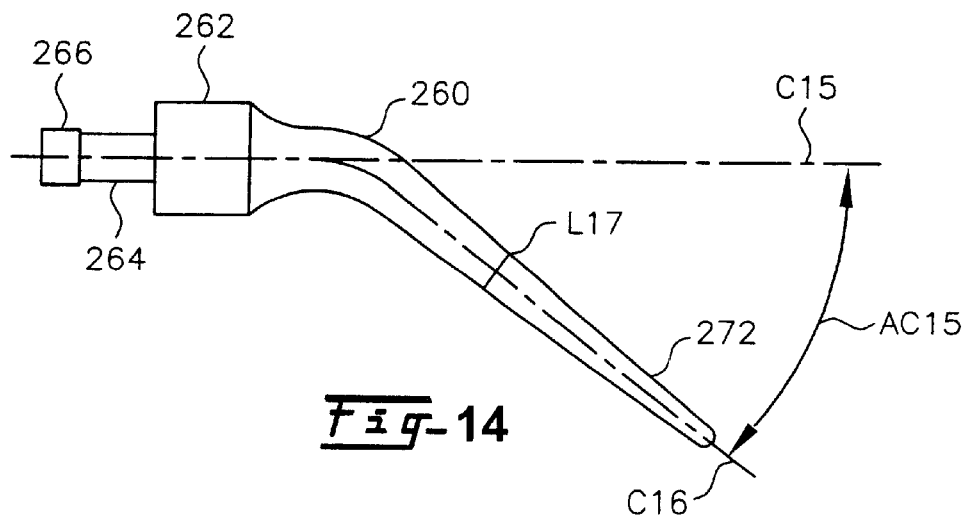
FIG. 14 is a side view of a subgingival tip in accordance with a preferred embodiment of the invention.
Figure 15:
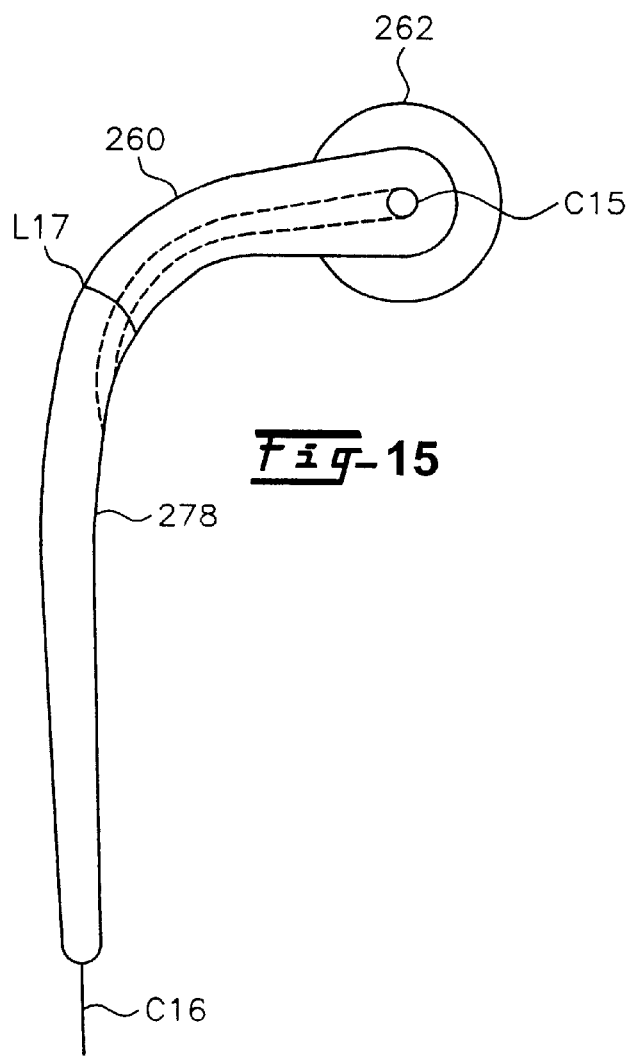
FIG. 15 is an end view of the tip shown in FIG. 14.

With more particular reference to FIGS. 14 and 15 subgingival tip 260 is seen. Tip 260 has step L17, flange 262 joined by connecting member 264 to flange 266. Step L17 is formed as disclosed by Dao et al in U.S. Pat. No. 5,749,727. Tip central axis $C15$ intersects central axis $C16$ of an internal passageway at angle $AC15$. Step L17 intersects passageway wall 278 at an edge which forms an orifice. Tip 260 is preferably made by bending a first bend, drilling and bending a second bend as discussed above in reference to FIGS. 4–9, then bending a third bend to form the shape shown in FIGS. 14 and 15.

Figure 16:
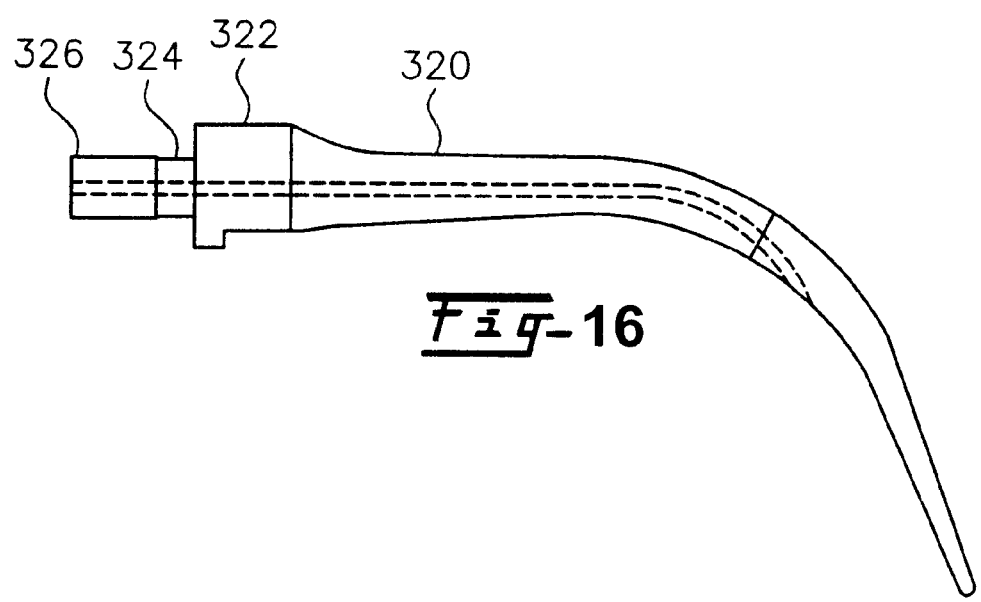
FIG. 16 is a side view of a tip having a fluid passageway having a centerline which is offset and parallel to the tip centerline in accordance with a preferred embodiment of the invention.

With more particular reference to FIG. 16 subgingival tip 320 is seen. Tip 320 has a fluid passageway having a centerline which is offset and parallel to the tip centerline. Tip 320 has flange 322 joined by connecting member 324 to flange 326. Initially tip 320 is solid metal and extends along a linear central axis as shown in FIG. 4. Then tip 320 is bent as shown in FIG. 5. A passageway is then drilled parallel to the linear portion of the central axis of tip 320. Then tip 320 is bent in the opposite direction as shown in FIG. 16.

In a preferred embodiment of the invention tip 320 has upper body end joined along shoulder (or step) to lower body end. The shoulder has a curved side wall. Preferably the step intersects the passageway wall edge which forms an orifice.

It is clear from the invention that the nature of the device activating the tool longitudinally is not a limitation. The tool may be electronically activated by means of electro-magnetostrictive elements as discussed or piezo electric crystals or other means, including air or water activation. While the preferred embodiment of the invention focuses upon use of the tool for dental operations, such as cleaning and scaling, it is intended that the instrument have broad use and application wherever it is desirable to act on a tooth surface with a vibratory motion with simultaneously providing fluid to irrigate the tip and tooth surfaces. The exact dimensions of the tip are determined by the operation for which the tip is employed. A typical tip shank diameter is 0.065 inches (1.65 mm) for certain dental application, such that the tip end can be tapered to a diameter small enough to fit into narrow crevices and areas between teeth. The exact location of the discharge orifice of the fluid is determined by many factors, including the frequency of operation as well as the transducer employed.

The nature of the fluid delivered to the tooth is dependent upon the operation to be performed on or at the tooth. In a dental cleaning environment, water is a useful fluid for cooling and removal of debris. In other uses it may be preferred to employ a saline solution, sterile water or a solution containing some selected medicament to achieve a particular purpose.

The nature of the passageway drilled within the tip is not critical. Conventionally, it will be a straight, linear bore. However, it is within the scope of the invention if a bore is curved. The essence of the invention is to establish a discharge orifice that maximizes the amount of material or metal remaining at or on the tip end for flexural strength while providing an orifice location with respect to the tip motion where spray is minimized.

The tip may be formed of any material that has sufficient strength under the longitudinal and flexural stresses to which it is subjected. Typically, a high strength stainless steel is utilized but the tip may be formed of engineered polymerics or other materials, such as carbon-filled polycarbonate, graphite composites or other materials that have sufficient hardness and elasticity to accommodate the motional stresses and wear of the operation.

It is noted that the tool tip of the invention is depicted in cross-section as cylindrical, tapering to a relatively small diameter and reduced to another taper angle to use in subgingival area. It is well known in the art that tools may have other configurations and cross-sections and such tools are within the scope of the invention. Whether the resulting tool tip is rectangular, irregular shaped or some other shape in cross-section or includes some configuration other than a tapered point at the working tip, it is preferred that the discharge exit be located adjacent to the flexural node where there is the lowest flexural motion and the orifice exit is least likely to cause fracture stresses in the tip. The discharge exit is preferably located distant from harmonic loops where motion is greatest. The discharge exit is preferably located overlapping not more than one harmonic loop. Such a loop is typically 7–9 mm from the tip end, for this preferred embodiment of this invention.

The particular characteristics of the shape of the tip, that is, bending radii, length of bent arc, length of section beyond the bend, tip tapers and the material from which the tip is fashioned, all contribute to the performance characteristics of the tip in flexure. The design of the tip, generally, and of the FIG. 4 tip in particular, utilizes the factors described above to provide a gain or amplification of the longitudinal vibrational motion produced by the insert, of from two to five fold.

The tip of the invention may be produced by a number of milling techniques. A preferred method first requires that the tip body is formed of cylindrical rod drawn to a diameter that is slightly larger than the finished tip diameter. The selected material is one that is corrosion resistant, of high tensile strength, high sheer strength, high fatigue limit, good toughness and that can be bent machined and/or formed. The rod is milled to substantially its final configuration before shaping and bending. The fluid passageway is formed in the tip body by means of a number of techniques including drilling and boring. Typically, after forming the passageway, the tip is machined, formed or bent to its useful finished shape and configuration.

A preferred boring method is by means of electric discharge machining (EDM), a process that insures that the passageway is angled to break out on a wall surface of the tip rod on the convex side of the existing or intended bend, preferably 5 to 14 mm from the end of the tip. In EDM, the passageway of a desired diameter is formed by a DC current that generates rapid repetitive spark discharges through a film of dielectric fluid flowing between the workpiece and a shaped electrode tool. An EDM system Model No. SP-1M, manufactured by Japan EDM Products, Division of Mitsui Machine Technology, Inc. of Glendale Heights, Ill., is employed to form 0.014 inch (0.36 mm) diameter fluid passageways for the tip of the invention.

Alternatively, the passageway is bored into the tip body or cylinder using a lathe that is equipped with a tail stock that can be offset. The offset is adjusted, for example, sufficient to produce an angle of 1 to 1.6 degrees from the centerline of the tip body cylinder. This is equivalent to an offset distance of 0.4 to 0.6 mm at the end of the cylinder. The passageway is drilled and the offset tailstock of the lathe is returned to its centering position, aligned with the live or driven center of the lathe. The blank is then machined, for example, to provide tapering, to its final design dimensions. The result will be a tip blank that has its internal fluid passageway centered at the large end of the blank and exiting at a cylindrical wall displaced from but near the small end of the tip. This process produces a blank that is of uniform cross-section taper at a larger angle typically 4°–6° and tapering again at smaller angle typically 2°–3° near the end of the tip, where vibrational stresses are greatest and maximum material within the design parameter is needed for strength. Maximum strength is achieved by this method because the machine tip blank has remained concentric to its maximum strength orientation formed along its longitudinal axis during drawing. The resulting tip will have a fluid outlet located 2 to 8 mm from the end of the tip.

Preferably the step circumscribes the tip from the passageway wall at one side of the orifice to the passageway wall at the other side of the orifice. Preferably the step is less than 3 mm wide, more preferably less than 1 mm wide and most preferably less than 0.5 mm wide. Preferably the lines are straight and at least from 1 mm in length.

Preferably the output portion of the tip is from 8 to 14 mm in length. That is the distance from the terminus of the tip to the step (the output portion) is preferably from 8 to 14 mm long. Most preferably the distance from the terminus of the tip to the step is from 9 to 11 mm in length.

The invention provides a transducer activated tool for contacting subgingival tooth surfaces and directing a fluid adjacent to the subgingival surfaces, comprising an activated tip having a fluid inlet end, a subgingival outlet end, and a fluid passageway wall internal to the tip. The fluid passageway wall has an average passageway diameter. The fluid passageway wall ends at an edge providing a fluid discharge orifice formed in a discharge side of the subgingival outlet end of the tip. The subgingival outlet end has an opposite side positioned opposite to the discharge side. The discharge side has a discharge side outer surface whereby a first line tangential to the discharge side outer surface of the fluid inlet end, and a second line tangential to the discharge side outer surface of the subgingival outlet end intersect to form an angle of less than 180 degrees facing outwardly from the discharge side outer surface. Preferably the fluid discharge orifice opens into a groove in the discharge side. The groove has a groove length less than three times as long as the average passageway diameter. Preferably the subgingival outlet end of the tip has an outer diameter less than 0.03 inch within 0.03 inch from the terminus of the subgingival outlet end. Preferably the subgingival outlet end is shaped to contact the tooth surfaces. Preferably the fluid discharge orifice has an orifice center and the orifice center is within 0.26 inch from the terminus of the subgingival outlet end.

The invention provides a transducer activated tool for contacting tooth surfaces and directing a fluid adjacent to the surfaces, comprising an activated tip having a fluid inlet end, a outlet end, and a fluid passageway wall internal to the tip, the activated tip having a tip centerline, the fluid passageway wall ends at an edge providing a fluid discharge orifice formed in a discharge side of the outlet end of the tip, the outlet end having an opposite side positioned opposite to the discharge side. The discharge side has a discharge side outer surface whereby a line uniformly offset from the tip centerline on the discharge side outer surface forms an angle of less than 180 degrees outwardly from the discharge side outer surface. The transducer activated tool is formed from a preformed body of the tool wherein the opposite side has an opposite side outer surface whereby a line uniformly offset from the tip centerline. on the opposite side outer surface forms an angle of less than 180 degrees outwardly from the opposite side outer surface, and a line uniformly offset from the tip centerline on the discharge side outer surface forms an angle of greater than 180 degrees outwardly from the discharge side outer surface. Preferably the tool is formed into a transducer activated subgingival tool by bending the preformed tool.

The invention provides a transducer activated subgingival tool for contacting subgingival tooth surfaces and directing a fluid adjacent to the surfaces, comprising an activated tip having a fluid inlet end, a subgingival outlet end, and a fluid passageway wall internal to the tip, the fluid passageway wall ends at an edge providing a fluid discharge orifice formed in a discharge side of the outlet end of the tip. The subgingival outlet end has an opposite side positioned opposite to the discharge side. The discharge side has a discharge side outer surface whereby a line on the discharge side outer surface forms an angle of less than 180 degrees outwardly from the discharge side outer surface. The transducer activated subgingival tool is formed from a preform of the tool. The opposite side has an opposite side outer surface whereby a line on the opposite side outer surface forms an angle of less than 180 degrees outwardly from the opposite side outer surface.

The invention provides a preformed tool for making a transducer activated subgingival tool for contacting subgingival tooth surfaces and directing a fluid adjacent to the surfaces, comprising an activated tip having a fluid inlet end, a subgingival outlet end, and a fluid passageway wall internal to the tip formed in the inlet end generally along the longitudinal center axis of the inlet end of the tip. The subgingival outlet end has a discharge side and an opposite side. The opposite side is opposite to the discharge side. The opposite side has an outer surface which forms an angle of less than 180 degrees. The fluid passageway has a central axis which is substantially on the center axis of the inlet end of the tip. The fluid passageway wall ends at an edge providing a fluid discharge orifice formed in the discharge side of the tip.

Preferably the preformed tool is formed into a transducer activated subgingival tool by bending the preformed tool so that the discharge side has an outer surface forms an angle of less than 180 degrees. Preferably the subgingival end of the tip is within 0.03 inch from the terminus of the subgingival outlet end and has an outer diameter less than 0.03 inch. Preferably the subgingival outlet end is shaped to contact the tooth surfaces, a step in the surface of the outer wall of the tip between the inlet end and the subgingival outlet end, an activating transducer connecting body connecting the tip to an activating transducer, the fluid passageway wall having an average diameter, the fluid passageway wall having an outlet opening diameter, the fluid passageway wall opening into a groove channel having a groove channel length, the groove channel length is more than 0.5 and less than three times the outlet opening diameter; and a fluid source connected to the tip fluid passageway and providing a flow of fluid discharging from the tip fluid passageway discharge orifice. Preferably the step intersects the passageway wall at the edge providing an orifice. Preferably a straight line parallel to and extending from the outer surface of the outer wall of the inlet end of the tip adjacent to the step intersects with the center axis forming a first angle with the center axis, a straight line parallel to and extending from the outer surface of the outer wall of the subgingival end of the tip adjacent to the step intersects with the center axis forming a second angle with the center axis, and the first angle is greater than the second angle by at least 0.25 degree and less than 5 degrees. Preferably a first line on, parallel to and extending from the outer surface of the outer wall of the inlet end of the tip adjacent to and within 3 mm of the step intersects with the center axis forming a first angle with the center axis, a second line on, parallel to and extending from the outer surface of the outer wall of the subgingival end of the tip adjacent to and within 3 mm of the step intersects with the center axis forming the first angle with the center axis, and the first and second lines are at least 0.1 mm apart at the step. Preferably the terminus of the outlet end of the tip has a centerline at the central axis of the tip at the terminus, and the step has a centerline at the central axis of the tip. Preferably the tip fluid passageway is angularly offset from the tip longitudinal center axis such that the fluid discharge orifice is formed in a lateral surface of the tip. Preferably the fluid discharge orifice has an orifice a centerline and the center point on the orifice centerline is about 0.01 to about 8 mm from the fluid outlet end of the tip. Preferably the activating transducer activates the tip by sonic, ultrasonic, fluid or air means and the activating transducer is a piezo crystal.

Preferably the discharge fluid is saline, water or a solution comprising a medicament. Preferably the tip is connected to the connecting body by threads, press fit, soldering, brazing or welding. Preferably the tip is formed of stainless steel, alloys, carbon filled polycarbonate or graphite composite material. Preferably the tip has a bend from its centerline axis through an arc of from about 60 to about 90 degrees.

A preferred embodiment of the invention provides an insert for an ultrasonically activated subgingival tool of a generally axially elongated cylindrical structure comprising a handpiece including a coil for generating an electromagnetic field, the insert is vibrated at high frequency in longitudinal motion in response to the coil, the insert comprising a magnetostrictive element; a connecting body, axially transmitting the high frequency motion from the ultrasonic magnetostrictive element; and a tip, axially attached to the connecting body, that receives the longitudinal motion, having distal surfaces shaped to contact a subgingival tooth surface. The tip comprises a fluid passageway wall extending internally through a substantial portion of the tip, formed generally along the longitudinal center axis of the tip, the tip having an inlet end and a subgingival outlet end, the subgingival end is shaped to contact the subgingival tooth surfaces without damaging the adjacent gum, a 0.03 inch length of the subgingival end of the tip within 0.03 inch of terminus having one or more outer diameters, each of the diameters is less than 0.03 inch. The fluid passageway wall has an average diameter, an outlet opening diameter, and opens into a groove channel having a groove channel length. The groove channel length is more than 0.5 and less than three times the outlet opening diameter. Preferably the inlet end and the subgingival outlet end extending in opposite directions from a step, the step is a topographical change in the outer surface of the tip, the input end and the output end each having one or more cross sectional dimensions, the longest cross-sectional dimension of the output end is smaller than the smallest cross-sectional dimension of the input end, the step intersects the passageway wall orifice. Preferably a line on the outer surface of the outer wall of the tip of the inlet end adjacent to the step forms a first angle with the center axis, a line on the outer surface of the outer wall of the tip of the subgingival outlet end adjacent to the step forms a second angle with the center axis, and the first angle in greater than the second angle. Preferably a line on the outer surface of the outer wall of the tip of the inlet end adjacent to and within 3 mm of the step forms a first angle with the center axis, a line on the outer surface of the outer wall of the tip of the subgingival end adjacent to and within 3 mm of the step forms the first angle with the center axis, and the lines are at least 0.1 mm apart at the step. Preferably the tip passageway orifice exits within a range of about 2–14 mm from the fluid outlet end of the tip. Preferably the passageway wall is offset from the axis such that a discharge orifice formed in the tip is displaced from the distal tip end center axis.

Preferably a fluid passageway is eccentrically offset from the tip axis, wherein the passageway is formed substantially parallel to the center axis of the tip but displaced therefrom. Preferably the passageway is displaced from the axis by about 0.1 to 0.5 mm. Preferably the discharge orifice is shaped such that the fluid flowing therefrom forms a desired pattern for contacting dental surfaces contacted by the tip.

A preferred embodiment of the invention provides a method of making an insert for an ultrasonically activated subgingival tooth cleaning tool, comprising providing a preformed tool comprising an activated tip having a fluid inlet end, a subgingival outlet end, and a fluid passageway wall internal to the tip, the fluid passageway wall ends at an edge providing a fluid discharge orifice formed in a discharge side of the tip, the fluid discharge orifice is in the discharge side, the tip having an opposite side, the opposite side is opposite to the discharge side, the opposite side having an outer surface which forms an angle of less than 180 degrees outwardly from the opposite side, bending the tip whereby a first line tangential to the discharge side outer surface of the fluid inlet end, and a second line tangential to the discharge side outer surface of the subgingival outlet end intersect to form an angle of less than 180 degrees facing outwardly from the discharge side outer surface. Preferably the fluid discharge orifice opens into a groove in the discharge side, the groove having a groove length, the groove length is less than three times as long as the average passageway diameter, the subgingival outlet end of the tip has an outer diameter less than 0.03 inch within 0.03 inch from the terminus of the subgingival outlet end, the subgingival outlet end is shaped to contact the tooth surfaces. Preferably the method of further comprises contacting a subgingival surface of the tooth adjacent to the gum covering the tooth surface with a transducer activated tool tip having an inlet end and a subgingival outlet end, and directing a fluid to the subgingival surface of the tooth and between the subgingival surface of the tooth and the gum in which the tooth is supported. Preferably the subgingival end extends distally from a step in the outer surface of the tip and is shaped to contact the tooth surfaces, the subgingival outlet end of the tip having a longest cross-sectional dimension of less than 0.03 inch; the passageway wall is offset from the centerline of the tip whereby a discharge orifice is formed by an edge of the passageway wall at a side of the tip and the step intersects the passageway wall orifice. Preferably a line on the outer surface of the outer wall of the tip of the inlet end adjacent to the step forms a first angle with the center axis, a line on the outer surface of the outer wall of the tip of the subgingival end adjacent to the step forms a second angle with the center axis, and the first angle in greater than the second angle. Preferably a line on the outer surface of the outer wall of the tip of the inlet end adjacent to and within 3 mm of the step forms a first angle with the center axis, a line on the outer surface of the outer wall of the tip of the subgingival end adjacent to and within 3 mm of the step forms the first angle with the center axis, and the lines are at least 0.1 mm apart at the step.

A preferred embodiment of the invention provides a method of making a transducer activated tool tip, comprising, providing a substantially linear tip body having a fluid inlet end and a fluid outlet end, bending the tip body in a first direction so that a centerline through the fluid outlet end intersects a centerline through the fluid inlet end at an angle greater than 5 degrees, and forming in the tip body a fluid passageway internal to the tip, having an inlet end and a subgingival outlet end, the subgingival outlet end of the tip having a longest cross-sectional dimension of less than 0.03 inch; bending the tip body in a second direction so that a centerline through the fluid outlet end intersects a centerline through the fluid inlet end at an angle of substantially 0 degrees, continuing to bend the tip body in the second direction so that the centerline through the fluid outlet end intersects the centerline through the fluid inlet end at an angle greater than 5 degrees.

A preferred embodiment of the invention provides a method of making a transducer activated tool tip for contacting subgingival tooth surfaces and directing a fluid adjacent to the surfaces, comprising, providing a substantially linear tip body having a fluid inlet end and a fluid outlet end, shaping the fluid outlet end to form distal surfaces for contacting the subgingival tooth surfaces; bending the tip body in a first direction so that a centerline through the fluid outlet end intersects a centerline through the fluid inlet end at an angle greater than 5 degrees, and forming in the tip body a fluid passageway internal to the tip, having an inlet end and a subgingival outlet end, the subgingival end extending distally from a step in the outer surface of the tip and is shaped to contact the tooth surfaces, the subgingival outlet end of the tip having a longest cross-sectional dimension of less than 0.03 inch; the passageway wall is offset from the centerline of the tip whereby a discharge orifice is formed by an edge of the passageway wall at a side of the tip, bending the tip body in a second direction so that a centerline through the fluid outlet end intersects a centerline through the fluid inlet end at an angle of substantially 0 degrees, continuing to bend the tip body in the second direction so that the centerline through the fluid outlet end intersects the centerline through the fluid inlet end at an angle greater than 5 degrees. Preferably the forming of the fluid passageway comprises electric discharge machining the passageway in a cylindrical rod, beginning at the center axis of an end of the rod and continuing at an angle of less than about 3 degrees from the center axis of the rod such that the passageway forms a discharge orifice 2–8 mm from the opposite, fluid outlet end of the rod. Preferably the shaping of the cylindrical rod into a desired shape for contacting subgingival tooth surfaces comprises machining and bending such that the fluid orifice is on a concave surface thereof to direct fluid adjacent or onto the tooth. Preferably the forming the tip fluid passageway, comprises securing a cylindrical rod in a lathe such that the tail end of the rod opposite the rod distal surfaces is offset from the longitudinal center axis of the lathe; and boring the rod such that the passageway forms a fluid discharge orifice 2–14 mm from the fluid outlet end of the tip. Preferably the tip fluid passageway orifice is eccentrically offset from the tip axis, wherein the passageway is substantially parallel to the center axis of the tip but displaced from the axis by 0.1 to 0.5 mm. Preferably the tip fluid outlet end is shaped to contact subgingival tooth surfaces and the fluid discharge orifice is located such that the fluid impinges upon the tooth surfaces. Preferably the step is a shoulder and the fluid discharge orifice intersects the shoulder. Preferably the tip further comprises a shoulder and the fluid discharge orifice intersects the shoulder.

A preferred embodiment of the invention provides a method of making a transducer activated tool tip for contacting subgingival tooth surfaces and directing a fluid adjacent to the surfaces, comprising, providing a substantially linear tip body has a fluid inlet end and a fluid outlet end, shaping the fluid outlet end to form distal surfaces for contacting the subgingival tooth surfaces; bending the tip body in a first direction so that a centerline through the fluid outlet end intersects a centerline through the fluid inlet end at an angle greater than 5 degrees, and forming in the tip body a fluid passageway internal to the tip, has an inlet end and a subgingival outlet end, the subgingival end extending distally from a step in the outer surface of the tip and is shaped to contact the tooth surfaces, the subgingival outlet end of the tip has a longest cross-sectional dimension of less than 0.03 inch; the passageway wall is offset from the centerline of the tip whereby a discharge orifice is formed by an edge of the passageway wall at a side of the tip, bending the tip body in a second direction so that a centerline through the fluid outlet end intersects a centerline through the fluid inlet end at an angle of substantially 0 degrees, continuing to bend the tip body in the second direction so that the centerline through the fluid outlet end intersects the centerline through the fluid inlet end at an angle greater than 5 degrees. The passageway wall offset from the centerline of the tip is formed as disclosed by Foulkes et al in U.S. Pat. No. 5,567,153, and the disclosure thereof is incorporated herein by reference in its entirety.

It will be apparent to those skilled in the art that various modifications and changes may be made in the practice and use of the present invention without departing from the scope thereof as set forth in the following claims.

What is claimed is:

1. A method of making an insert for an ultrasonically activated tooth cleaning tool, comprising:
    bending a solid metal tip to form a bend at a location for an opening of a passageway, and then
    drilling the passageway through said solid metal tip to form a tip having a passageway having a fluid discharge orifice at said bend.

2. A method of making a transducer activated tool tip, comprising,
    providing a substantially linear tip body having a fluid inlet end and a fluid outlet end,
    bending said tip body in a first direction so that a centerline through said fluid outlet end intersects a centerline through said fluid inlet end at an angle greater than 5 degrees, and
    forming in said tip body a fluid passageway internal to said tip, having an inlet end and a outlet end, said outlet end of said tip having a longest cross-sectional dimension of less than 0.03 inch;
    bending said tip body in a second direction so that a centerline through said fluid outlet end intersects a centerline through said fluid inlet end at an angle of substantially 0 degrees,
    continuing to bend said tip body in said second direction so that said centerline through said fluid outlet end intersects said centerline through said fluid inlet end at an angle greater than 5 degrees.

3. A method of making a transducer activated tool tip for contacting subgingival tooth surfaces and directing a fluid adjacent to said surfaces, comprising,
    providing a substantially linear tip body having a fluid inlet end and a fluid outlet end,
    shaping said fluid outlet end to form distal surfaces for contacting said subgingival tooth surfaces;
    bending said tip body in a first direction so that a centerline through said fluid outlet end intersects a centerline through said fluid inlet end at an angle greater than 5 degrees, and
    forming in said tip body a fluid passageway internal to said tip, having an inlet end and a subgingival outlet end, said subgingival end extending distally from a step in the outer surface of the tip and being shaped to contact said tooth surfaces, said subgingival outlet end of said tip having a longest cross-sectional dimension of less than 0.03 inch; said passageway wall being offset from the centerline of the tip whereby a discharge orifice is formed by an edge of said passageway wall at a side of said tip,
    bending said tip body in a second direction so that a centerline through said fluid outlet end intersects a centerline through said fluid inlet end at an angle of substantially 0 degrees,
    continuing to bend said tip body in said second direction so that said centerline through said fluid outlet end intersects said centerline through said fluid inlet end at an angle greater than 5 degrees.

4. The method of claim 3 wherein forming of said fluid passageway comprises electric discharge machining said passageway in a cylindrical rod, beginning at the center axis of an end of said rod and continuing at an angle of less than about 3 degrees from the center axis of said rod such that the passageway forms a discharge orifice 2–8 mm from the opposite, fluid outlet end of said rod.

5. The method of claim 3 wherein shaping of said cylindrical rod into a desired shape for contacting subgingival tooth surfaces comprises machining and bending such that said fluid orifice is on a concave surface thereof to direct fluid adjacent or onto said tooth.

6. The method of claim 3 wherein forming said tip fluid passageway, comprises:
    securing a cylindrical rod in a lathe such that the tail end of said rod opposite said rod distal surfaces is offset from the longitudinal center axis of the lathe; and
    boring said rod such that said passageway forms a fluid discharge orifice 2–14 mm from the fluid outlet end of said tip.

7. A method of making an insert for an ultrasonically activated tooth cleaning tool, comprising:
    bending a solid metal tip preform to form a bend at a location for an opening of a passageway, and then drilling the passageway through said solid metal tip preform to form a drilled tip having a passageway having a fluid discharge orifice at said bend.

8. The method of claim 7 wherein said fluid discharge orifice is on a discharge side of said tip, said tip has an opposite side, said opposite side is opposite to said discharge side and further comprising bending said drilled tip whereby a first line tangential to said discharge side outer surface of a fluid Inlet end, and a second line tangential to said discharge side outer surface of an outlet end intersect to form an angle of less than 180 degrees facing outwardly from said discharge side outer surface.

9. The method of claim 7 wherein said drilled tip comprises a fluid inlet end, a subgingival outlet end, and a fluid passageway wall internal to said drilled tip, said fluid passageway wall ends at an edge providing a fluid discharge orifice formed in a discharge side of said tip, said fluid discharge orifice being in said discharge side, said tip having an opposite side, said opposite side being opposite to said discharge side, said opposite side having an outer surface which forms an angle of less than 180 degrees outwardly from said opposite side, bending said tip whereby a first line tangential to said discharge side outer surface of said fluid inlet end, and a second line tangential to said discharge side outer surface of said subgingival outlet end intersect to form an angle of less than 180 degrees facing outwardly from said discharge side outer surface.

10. The method of claim 9 wherein said fluid discharge orifice opens into a groove in said discharge side, said groove having a groove length, said groove length being less than three times as long as said average passageway diameter, said subgingival outlet end of said tip has an outer diameter less than 0.03 inch within 0.03 inch from tee terminus of said subgingival outlet end, said subgingival outlet end being shaped to contact subgingival tooth surfaces.

11. The method of claim 9 further comprising contacting a subgingival surface of a tooth adjacent to the gum covering said tooth surface with a transducer activated tool tip having an inlet end and a subgingival outlet end, and directing a fluid to said subgingival surface of said tooth and between said subgingival surface of said tooth and the gum in which said tooth is supported.

12. The method of claim 9 wherein said subgingival end extends distally from a step in the outer surface of me tip and being shaped to contact said tooth surfaces, said subgingival outlet end of said tip having a longest cross-sectional dimension of less than 0.03 inch; said passageway wall being offset from the centerline of the tip whereby a discharge orifice is formed by an edge of said passageway wall at a side of said tip and said step intersects said passageway wall orifice.

13. The method of claim 9 wherein a line on the outer surface of said outer wall of said tip of said inlet end adjacent to a step forms a first angle with said center axis, a line on the outer surface of said outer wall of said tip of said subgingival end adjacent to said step forms a second angle with said center axis, and said first angle in greater than said second angle.

14. The method of claim 9 wherein a line on the outer surface of said outer wall of said tip of said inlet end adjacent to and within 3 mm of a step forms a first angle with said center axis, a line on the outer surface of said outer wall of said tip of said subgingival end adjacent to and within 3 mm of said step forms said first angle with said center axis, and said lines are at least 0.1 mm apart at said step.

15. A preformed tip for making a transducer activated subgingival tool for contacting subgingival tooth surfaces and directing a fluid adjacent to said surfaces, said preformed tip comprising:

a substantially linear body portion having a fluid inlet end, a subgingival outlet end, and a substantially linear fluid passageway wall internal to said substantially linear body portion, said passageway wall extending from said inlet end along a substantially linear longitudinal center axis of said substantially linear body portion to a fluid discharge orifice formed in a discharge side of said preformed tip, said preformed tip having an opposite side, said opposite side being opposite to said discharge side, said opposite side having an outer surface, said opposite side outer surface bending away from said discharge side, said opposite side outer surface forming an angle of less than 180 degrees, said discharge side having an outer surface, said discharge side outer surface forming an angle of greater than 180 degrees.

16. The preformed tip of claim 15 formed into a transducer activated subgingival tool by bending said preformed tool so that said discharge side outer surface forms an angle of less than 180 degrees.

17. The preformed tip of claim 15 wherein said discharge side outer surface does not intersect said substantially linear longitudinal center axis, and said subgingival end of said tip within 0.03 inch from the terminus of said subgingival outlet end having an outer diameter less than 0.03 Inch, said subgingival outlet end being shaped to contact said tooth surfaces, a step in the surface of the outer wall of said tip between said inlet end and said subgingival outlet end, an activating transducer connecting body connecting said tip to an activating transducer, said fluid passageway wall having an average diameter, said fluid passageway wall having an outlet opening diameter, said fluid passageway wall opening into a groove channel having a groove channel length, said groove channel length being more than 0.5 and less than three times said outlet opening diameter, and a fluid source connected to said tip fluid passageway and providing a flow of fluid discharging from said tip fluid passageway discharge orifice.

18. The tip of claim 15 wherein a straight line parallel to and extending from the outer surface of said outer wall of said Inlet end of said tip adjacent to said step intersects with said center axis forming a first angle with said center axis, a straight line parallel to and extending from the outer surface of said outer wail of said subgingival end of said tip adjacent to said step intersects with said center axis forming a second angle with said center axis, and said first angle is greater than said second angle by at least 0.25 degree and less than 5 degrees.

19. The tip of claim 15 wherein a first line on, parallel to and extending from the outer surface of said outer wall of said Inlet end of said tip adjacent to and within 3 mm of said step Intersects with said center axis forming a first angle with said center axis, a second line on, parallel to and extending from the outer surface of said outer wall of said subgingival end of said tip adjacent to and within 3 mm of said step intersects with said center axis forming said first angle with said center axis, and said first and second lines are at least 0.1 mm apart at said step.

20. The tip of claim 15 wherein the terminus of said outlet end of said tip has a centerline at the central axis of said tip at said terminus, and said step has a centerline at the central axis of said tip.

21. The tip of claim 15 wherein said tip fluid passageway is angularly offset from the tip longitudinal center axis such that said fluid discharge orifice is formed in a lateral surface of said tip.

22. The tip of claim 15 wherein said fluid discharge orifice has an orifice a centerline and the center point on said orifice centerline is about 0.01 to about 8 mm from the fluid outlet end of said tip.

23. The tip of claim 15 wherein said activating transducer activates said tip by sonic, ultrasonic, fluid or air means and said activating transducer is a piezo crystal.

24. The tip of claim 15 wherein said discharge fluid is saline, water or a solution comprising a medicament.

25. The tip of claim 15 wherein said tip is formed of stainless steel alloys, carbon filled polycarbonate or graphite composite material.

26. The tip of claim 15 wherein said tip has a bend from its centerline axis through an arc of from about 60 to about 90 degrees.

* * * * *